United States Patent [19]

Muraoka

[11] Patent Number: 5,480,460
[45] Date of Patent: Jan. 2, 1996

[54] METHOD FOR IMPROVING THE STABILITY IN AIR OF A HAIR DYE CONCENTRATE

[75] Inventor: Tsutomu Muraoka, Tokyo, Japan

[73] Assignee: Kao Corporation, Tokyo, Japan

[21] Appl. No.: 292,047

[22] Filed: Aug. 18, 1994

Related U.S. Application Data

[63] Continuation of Ser. No. 881,320, May 7, 1992, abandoned, which is a continuation of Ser. No. 557,851, Jul. 26, 1990, abandoned.

[30] Foreign Application Priority Data

Jul. 27, 1989 [JP] Japan .................................. 1-194473

[51] Int. Cl.$^6$ ...................................... A61K 7/13
[52] U.S. Cl. ............................ 8/416; 8/405; 8/406; 8/423
[58] Field of Search ............................... 8/405, 406, 408, 8/409, 410, 411, 416, 423, 428, 429, 432, 435, 527, 528; 424/70

[56] References Cited

U.S. PATENT DOCUMENTS

| | | | |
|---|---|---|---|
| 3,950,127 | 4/1976 | Halasz et al. | 8/414 |
| 3,951,589 | 4/1976 | Alperin et al. | 8/415 |
| 3,977,826 | 8/1976 | Iscowitz | 8/416 |
| 3,986,825 | 10/1976 | Sokol | 8/406 |
| 4,019,858 | 4/1977 | Conger, Sr. | 8/527 |
| 4,021,486 | 5/1977 | Halasz et al. | 8/414 |
| 4,152,112 | 5/1979 | Bugaut et al. | 8/416 |
| 4,333,730 | 6/1982 | Bugaut et al. | 8/416 |
| 4,713,080 | 12/1987 | Konrad et al. | 8/408 |
| 4,961,925 | 10/1990 | Tsujino et al. | 8/406 |
| 4,975,092 | 12/1990 | Chan et al. | 8/408 |
| 5,073,173 | 12/1991 | Pan et al. | 8/405 |

FOREIGN PATENT DOCUMENTS

| | | |
|---|---|---|
| 0352375 | 1/1990 | European Pat. Off. . |
| 2508055 | 6/1981 | France . |

OTHER PUBLICATIONS

Patent Abstracts of Japan, Jul. 29, 1978, Abstract of Kokai No. 53-59051.

*Primary Examiner*—Paul Lieberman
*Assistant Examiner*—Caroline L. Dusheck
*Attorney, Agent, or Firm*—Sughrue, Mion, Zinn, Macpeak & Seas

[57] ABSTRACT

A dye concentrate for dyeing keratin fibers which comprises the following components (A), (B) and (C):

(A) 10% by weight or more, based on the total weight of the composition, of an oxidation dye having two or more amino groups per molecule in the non-salt form or salt free;

(B) 0.5% by weight or more, based on the total weight of the composition, of an inorganic or organic reducing agent; and (C) water or an organic solvent;

and a dye composition for dyeing keratin fibers containing the same are disclosed. The dye concentrate of the present invention remains stable even when stored for a long time and can be easily formulated into a dye composition at use.

5 Claims, No Drawings

METHOD FOR IMPROVING THE STABILITY IN AIR OF A HAIR DYE CONCENTRATE

This is a Continuation of application Ser. No. 07/881,320 filed May 7, 199, now abandoned, in turn a Continuation of application Ser. No. 07/557,851 filed Jul. 26, 1990, now abandoned.

FIELD OF THE INVENTION

This invention relates to a dyeing composition for keratin fibers. More particularly, it relates to a dye concentrate for dyeing keratin fibers (which will sometimes be simply called a "dye concentrate" hereinafter) which is stable even if stored for a long time and from which a dye composition for dyeing keratin fibers (which will sometimes be simply called a "dye composition" hereinafter) can be prepared, and to a dye composition containing the same.

BACKGROUND OF THE INVENTION

Among oxidation dyes commonly used in oxidation hair dyes, those having two or more amino groups per molecule (for example, toluene-2,5-diamine, p-phenylenediamine, m-phenylenediamine) are disadvantageous in that they are liable to be oxidized by oxygen in the air. As a result, these dyes suffer from a decrease in purity or assume a black or tar-like appearance upon storage, which makes them unsuitable for use.

In order to improve the stability of these oxidation dyes, it has been attempted to use them in the form of salts, such as sulfates or hydrochlorides. Since oxidation dyes are generally used under neutral or alkaline conditions, however, it is necessary to neutralize such a dye in the form of a salt by adding a basic material to such a dye composition. This neutralization step results in the formation of a large amount of salt which lowers the solubility of other components (for example, dyes, oils) or lowers the emulsification stability of the composition. Thus, the formulation of such a dye composition is greatly restricted.

Accordingly, it has been required to use such a dye not in the form of a salt but in the non-salted form or salt free form to improve the stability thereof.

On the other hand, it is very convenient to prepare a concentrate of such a dye which can be easily formulated into a dye composition at use. However, the art has not believed it to be practically possible to prepare such a concentrate since said dye is highly unstable, as earlier described.

Under these circumstances, we conducted extensive studies in order to solve the above-mentioned problems. As a result, we found that a dye concentrate can be obtained by blending such a dye in the non-salt form or salt free form with a reducing agent, thus reaching the present invention.

SUMMARY OF THE INVENTION

The present invention provides a dye concentrate for dyeing keratin fibers which comprises the following components (A), (B) and (C):

(A) 10% by weight or more, based on the total weight of the composition, of an oxidation dye having two or more amino groups per molecule in the non-salt form or salt free form;

(B) 0.5% by weight or more, based on the total weight of the composition, of an inorganic or organic reducing agent; and (C) water or an organic solvent.

Further, the present invention provides a dye composition for dyeing keratin fibers which comprises the dye concentrate.

DETAILED DESCRIPTION OF THE INVENTION

Examples of the oxidation dye, i.e., component (A) used in the present invention, include an aromatic amino compound and a heterocyclic compound, each having two or more amino groups per molecule of the non-salt form or salt free form. Specific examples thereof include toluene-2,5-diamine, p-phenylenediamine, m-phenylenediamine and 2,6-diaminopyridine. The content of component (A) in the dye concentrate may be 10% (by weight based on the total weight of the composition, the same will apply hereinafter) or more, preferably from 10 to 50%, taking the workability and stability of the dye concentrate into consideration. When the content of component (A) exceeds 50%, the cold stability of the obtained system is lowered.

Examples of the reducing agent, i.e., component (B) include salts of sulfurous acid, salts of hydrogensulfurous acid, ascorbic acid, salts of ascorbic acid, erythrobic acid, thioglyolic acid, salts of thioglycollic acid, L-cysteine and cysteine derivatives such as N-acetyl-L-cysteine, L-cysteine methyl ester and L-cysteine ethyl ester. The term "salts" as used herein preferably includes alkali metal salts and ammonium salts.

Among these reducing agents, particularly preferable examples are sodium sulfite, ascorbic acid, thioglycolic acid and ammonium thioglycolate. The content of the reducing agent may be 0.5% or above, preferably from 0.5 to 5%. When the content of the reducing agent is less than 0.5%, the dye exhibits insufficient stability and suffers from a deterioration in performance and coloration with the lapse of time. When it exceeds 5%, on the other hand, the stability of the resulting system is lowered.

The solvent, i.e., component (C), may vary depending on the reducing agent used. When an inorganic reducing agent is used, water is preferably selected as the solvent. When an organic reducing agent is used, the solvent may be preferably selected from among straight or branched lower alcohols having 1 to 4 carbon atoms (for example, ethanol, propanol, isopropanol); and alkylene glycols having 2 to 6 carbon atoms (for example, ethylene glycol, propylene glycol, butylene glycol). The content of the solvent may preferably range from 45 to 89.5%. When the content thereof is less than 45%, the stability of the system obtained is poor. When it exceeds 89.5%, on the other hand, the stability of the dye is deteriorated and the dye concentration is lowered.

Components (A) to (C) may be preferably blended at the following weight ratios:

B/A: from 0.01 to 0.5, more preferably from 0.02 to 0.5,

C/A: from 0.90 to 8.95, more preferably from 0.98 to 8.90,

C/B: from 10 to 150, more preferably from 15 to 89.

When the B/A ratio is less than 0.01, the dye cannot be sufficiently stabilized. As a result, the product suffers from serious coloration with the lapse of time and thus the performance thereof is deteriorated. When the C/A ratio is less than 0.90 the C/B ratio is less than 10, the cold stability of the system is poor and the dye and reducing agent precipitate. When the B/A ratio exceeds 0.5, the stability of the system is lowered. When the C/A ratio exceeds 8.95 or the C/B ratio exceeds 150, the stability of the dye becomes insufficient.

The dye concentrate of the present invention may be prepared by mixing the above-mentioned components (A) to (C) so as to obtain a paste or a solution. When the dye concentrate is to be formulated into a dye composition, various additives commonly used in dye compositions (for example, thickeners, UV absorbers, antioxidants, preservatives, pearling agents, stabilizers, solubilizers, penetrants, emulsifiers, wetting agents, colorants, perfumes, vaseline, liquid paraffins, ester oils, alcohols, polyhydric alcohols, fatty acids) may be optionally added.

As described above, the dye concentrate of the present invention remains stable even when stored for a long time. Further, it may be easily formulated into a dye composition at use without any restriction. Furthermore, the concentrate, which is in the form of a solution or a paste, will not cause staining due to scattering.

To further illustrate the present invention, and not by way of limitation, the following Example is given.

EXAMPLE

Dye concentrates of the compositions as given in Table 1 were stored and the dye concentrations and changes in the appearances of the dye concentrates were monitored. Further, each dye concentrate was added to a Hair dye cream base 1 of the following composition and performance of the dye product thus obtained was examined by the following manner. Table 1 shows the results.

Stability

The dye product thus obtained was stored at 40° C. for 1 month and the remaining dye concentration was measured by liquid chromatography. The remaining dye concentration thus measured was converted to a relative value per the dye concentration of the product before being stored and the relative remaining ratio of dye was evaluated in the following criterion.

A: 80% or more.
B: 80 to 60%.
C: less than 60%.

Change in Appearance

Changes in color and form of the dye product after being stored at 40° C. for 1 month compared to those of the product being before stored were visually observed and evaluated in the following criterion.

A: no change in color or form.
B: serial change in color or form.

Workability

Workability of the dye product was evaluated in the following criterion.

A: no flying of dye.
B: scattering of dye.

Stability

Stability of the product after being stored at 40° C. for 1 month was evaluated in the following criterion.

A: good.
B: bad.

| Hair dye cream base 1 | (% by weight) |
|---|---|
| *toluene-2,5-diamine | 2.0 |
| resorcinol | 0.5 |
| m-aminophenol | 0.5 |
| polyoxyethylene (20EO) cetyl ether | 5.0 |
| stearyltrimethylammonium chloride | 1.0 |
| 2-hexyldecyltrimethylammonium chloride | 0.2 |
| 2-dodecylhexadecyl alcohol | 0.8 |
| cetostearyl alcohol | 5.0 |
| propylene glycol | 8.0 |
| liquid paraffin | 1.0 |
| methylparaben | 0.2 |
| ammonium thioglycolate | 0.2 |
| aqueous ammonia (28%) | 8.0 |
| perfume | 0.3 |
| purified water | balance |
| Total | 100.0 |

Invention products 1 to 3 and the comparative products 1 to 3 were each added to the Hair dye cream base 1 in such an amount as to give a toluene-2,5-diamine (active ingredient) content in the base of 2.0%.

TABLE 1

| Composition | Comparative product 1 | Comparative product 2 | Product of the Invention 1 | Product of the Invention 2 | Product of the Invention 3 | Comparative product 3 |
|---|---|---|---|---|---|---|
| toluene-2,5-diamine | 100 | — | 30 | 40 | 20 | 30 |
| toluene-2,5-diamine sulfate | — | 100 | — | — | — | — |
| sodium sulfite | — | — | 3 | — | 2 | 0.25 |
| ammonium thioglycolate | — | — | — | 1 | — | — |
| ascorbic acid | — | — | — | — | 1 | — |
| propylene glycol | — | — | — | 59 | — | — |
| purified water | — | — | 67 | — | 77 | 69.75 |
| Stability at 40° C. for 1 month (decrease in dye concentration) | C | A | A | A | A | C |
| Change in appearance at 40° C. for 1 month for 1 month | B (Dark brown and partially tar-like) | A | A | A | A | B (Dark brown and opaque solution) |
| Workability | B | B | A | A | A | A |

TABLE 1-continued

| Composition | Comparative product | | Product of the Invention | | | Comparative product |
|---|---|---|---|---|---|---|
| | 1 | 2 | 1 | 2 | 3 | 3 |
| Stability of product (40° C., 1 month) | (Scattering of dye) A | (Scattering of dye) B (Separated) | A | A | A | A |

While the invention has been described in detail and with reference to specific examples thereof, it will be apparent to one skilled in the art that various changes and modifications can be made therein without departing from the spirit and scope thereof.

What is claimed is:

1. A method for improving the stability in the air of a hair dye concentrate for keratin fibers consisting essentially of an oxidation dye having two or more amino groups per molecule in the non-salt or salt free form, wherein said oxidation dye is selected from the group consisting of toluene-2,5-diamine, p-phenylenediamine, m-phenylenediamine, and 2,6-diaminopyridine, and water or an organic solvent, which method comprises adding an inorganic or organic reducing agent selected from the group consisting of salts of sulfurous acid, salts of hydrogensulfurous acid, ascorbic acid, salts of ascorbic acid, erythrobic acid, thioglycolic acid, salts of thyoglycolic acid, and cysteine derivatives to the hair dye concentrate, wherein the content of the oxidation dye is from about 20% to 50% by weight, based on the total weight of the composition, the content of the reducing agent is from 0.5% to 5% by weight, based on the total weight of the composition, the content of the water or organic solvent is from 45 to 89.5% by weight, based on the total weight of the composition, and wherein the weight ratio of the reducing agent to the oxidation dye is from 0.01 to 0.5, the weight ratio of the water or organic solvent to the oxidation dye is from 0.90 to 8.95 and the weight ratio of the water or organic solvent to the reducing agent is from 10 to 150.

2. The method of claim 1, which further comprises allowing said hair dye concentrate to stand in contact with the air.

3. The method of claim 1, wherein said solvent is water.

4. The method of claim 1, wherein said solvent is said organic solvent.

5. The method of claim 4, wherein said solvent is a lower alcohol or alkylene glycol.

* * * * *